United States Patent [19]

Stütz et al.

[11] 4,146,626
[45] Mar. 27, 1979

[54] 8-ADAMANTYLAMINOMETHYL ERGOLENE DERIVATIVES

[75] Inventors: Peter Stütz, Vienna, Austria; Paul Stadler, Biel-Benken, Switzerland

[73] Assignee: Sandoz Ltd., Basel, Switzerland

[21] Appl. No.: 860,308

[22] Filed: Dec. 14, 1977

[30] Foreign Application Priority Data

Dec. 16, 1976 [CH] Switzerland ............... 15820/76

[51] Int. Cl.² ............... C07D 457/02; A61K 31/48
[52] U.S. Cl. ............................. 424/261; 546/67
[58] Field of Search ............... 260/285.5; 424/261

[56] References Cited

U.S. PATENT DOCUMENTS 3,228,942  1/1966  Camerino et al. ............... 260/285.5

FOREIGN PATENT DOCUMENTS 985004  3/1965  United Kingdom ............... 260/285.5

*Primary Examiner*—Donald G. Daus
*Assistant Examiner*—M. Lee
*Attorney, Agent, or Firm*—Gerald D. Sharkin; Robert S. Honor; Thomas O. McGovern

[57] ABSTRACT

The present invention provides compounds of the formula,

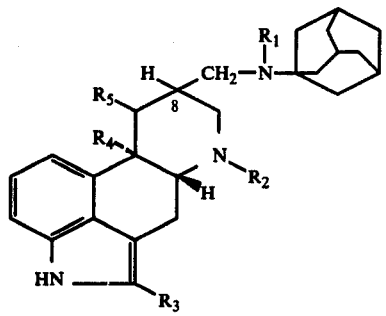

wherein
$R_1$ is alkyl ($C_{1-5}$),
$R_2$ is alkyl ($C_{1-5}$),
$R_3$ is hydrogen or halogen, and either each of $R_4$ and $R_5$ is hydrogen, or
$R_4$ and $R_5$, together, are a bond, which are useful as sleep-inducing and sleep-prolonging agents.

7 Claims, No Drawings

8-ADAMANTYLAMINOMETHYL ERGOLENE DERIVATIVES

The invention relates to ergot derivatives.

The present invention provides compounds of formula I,

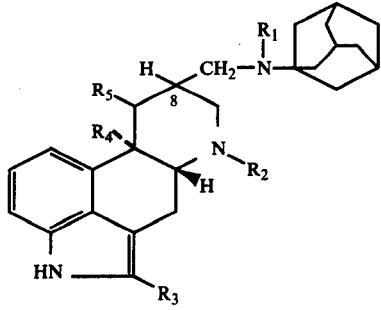

wherein
- $R_1$ is alkyl ($C_{1-5}$),
- $R_2$ is alkyl ($C_{1-5}$),
- $R_3$ is hydrogen or halogen, and either each of $R_4$ and $R_5$ is hydrogen, or
- $R_4$ and $R_5$, together, are a bond.

In formula I the side chain in the 8 position of the ergoline or ergolene nucleus may have the α or β configuration. Preferably it has the β configuration.

Preferably $R_1$ has 2 carbon atoms or more preferably 1 carbon atom.

Preferably $R_2$ is methyl or isopropyl.

When $R_3$ is halogen, this is fluorine, bromine or chlorine, preferably chlorine or bromine. Conveniently $R_3$ is hydrogen.

Preferably $R_4$ and $R_5$ are together a bond.

The present invention provides a process for the production of a compound of formula I which comprises a. condensing a compound of formula II,

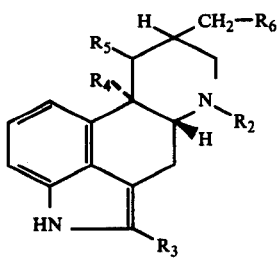

wherein
- $R_2$, $R_3$, $R_4$ and $R_5$ are as defined above, and
- $R_6$ is a leaving group, with a compound of formula III,

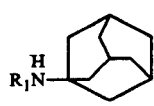

wherein $R_1$ is as defined above, b. reducing a compound of formula IV,

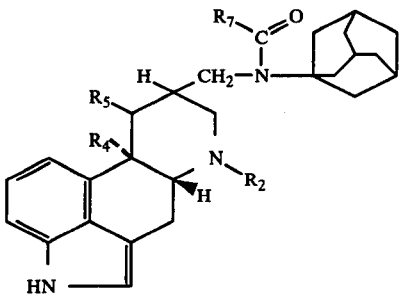

wherein
- $R_2$, $R_4$ and $R_5$ are as defined above, and
- $R_7$ is hydrogen or alkyl of 1 to 4 carbon atoms, to produce a compound of formula I',

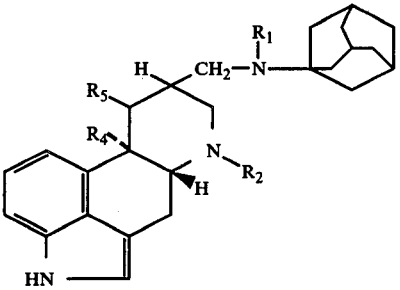

wherein $R_1$, $R_2$, $R_4$ and $R_5$ are as defined above, or c. hydrogenating a compound of formula I', as defined above wherein $R_4$ and $R_5$, together, are a bond, to produce a compound of formula I'',

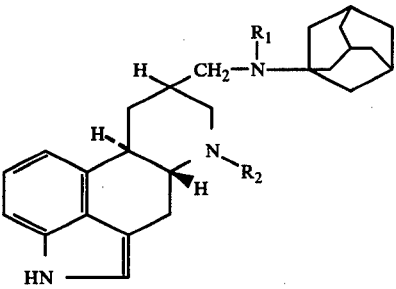

wherein $R_1$ and $R_2$ are as defined above.

The condensation according to process (a) may be effected in conventional manner for condensation reactions to produce analogous compounds. $R_6$ is preferably mesyloxy. The reaction may be effected at from 50° 1 to 180° C.

The reduction according to process (b) may be effected in conventional manner for the selective reduction of an amide, e.g. with lithium aluminium hydride or sodium dihydro-bis-(2-methoxyethoxy)-aluminate.

The hydrogenation according to process (c) may be effected in conventional manner for the hydrogenation of an ergolene to an ergoline. A catalyst such as palladium-on-charcoal is preferably used.

In any of the above processes, especially process (a), when an ergolene starting material is used, some isomerization may occur at the 8-position, resulting in the production of both 8α and 8β isomeric final products.

The starting materials are known or may be made in conventional manner as described in the Examples.

For example, a compound of formula IV may be produced by i. reacting a compound of formula II wherein $R_3$ is hydrogen and $R_4$ and $R_5$ together are a bond with 1-adamantylamine to produce a compound of formula V,

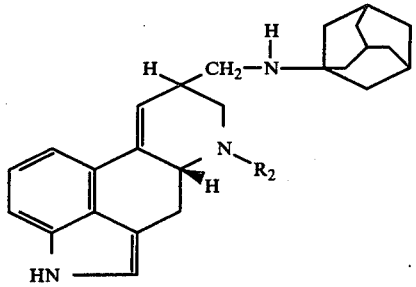  V and ii. acylating the resultant compound of formula V with an acid anhydride or chloride.

Free base forms of compounds of formula I may be converted into acid addition salt forms in conventional manner and vice versa. A suitable acid is hydrochloric acid, maleic acid or malonic acid.

In the following Examples, all temperatures are in degrees Centigrade and are uncorrected.

EXAMPLE 1

N-methyl-N-(6-methyl-8α or β-ergolenylmethyl)-1-adadamantylamine [process a)]

106.4 g Lysergol mesylate (dried at 60° in a high vacuum), 105.6 g N-methyl-1-adamantylamine in 2000 ml absolute dimethylformamide are maintained at 150° for 1.5 hours. After cooling, the mixture is evaporated in a vacuum. The residue is taken up in methylene chloride. The mixture is extracted with 10% tartaric acid and water. The combined aqueous acidic extracts are made alkaline with ammonia and then continuously extracted with methylene chloride. The organic extract is evaporated and the residue is chromatographed on silicagel twice eluting, a. with methylene chloride, the 8α title compound in free base form. M.Pt. 93°–95°; $[\alpha]_D^{20} = +76°$ (c = 0.5, pyridine), and b. with methylene chloride + 2.5 to 5% (v/v) methanol, the 8β title compound isomer in free base form. M.Pt. 230° (decomp.); $[\alpha]_D^{20} = +52.3°$ (c = 1, pyridine). Bis(base)maleate. M.Pt. 150°–152°; $[\alpha]_D^{20} = +63°$ [c = 0.57 in 50% (v/v) aqueous ethanol]. Bis(base)malonate demihydrate. M.Pt. 171°–172°; $[\alpha]_D^{20} = +69°$ [c = 0.49 in 50% (v/v) aqueous ethanol].

EXAMPLE 2

N-methyl-N-(6-methyl-8β-ergolenylmethyl)-1-adamantylamine [process b)]

12.3 g N-formyl-N-(6-methyl-8β-ergolenylmethyl)-1-adamantylamine in 800 ml absolute tetrahydrofuran are added dropwise to a suspension of 18 g lithium aluminium hydride in 500 ml tetrahydrofuran over 30 minutes at room temperature. The mixture is stirred for a further 2 hours at 20°. The mixture is cooled to 0° and a mixture of 40 ml water and 40 ml tetrahydrofuran is added with stirring. The mixture is stirred for a further 30 minutes. The precipitate is filtered off and the precipitate washed three times with methylene chloride containing a little ethanol. The combined filtrates are evaporated to give a crystalline product which is crystallized three times from methylene chloride/methanol, to give the title compound in free base form; M.Pt. 230° (decomp); $[\alpha]_D^{20} = +52.3°$ (c = 1, pyridine). Salt forms — see Example 1.

The starting material may be obtained as follows:

a. N-(6-methyl-8β-ergolenyl methyl)-1-adamantylamine 26.6 g lysergol mesylate and 60.5 g 1-adamantylamine in 160 ml absolute dimethylformamide are warmed at 60° for 48 hours. The cooled mixture is worked up in analogous manner to Example 1, ending with chromatography on aluminium oxide and then recrystallization twice from methylene chloride/methanol. The heading compound in free base form crystallizes as trapezoid leaves; M.Pt. 210° (decomp.), $[\alpha]_D^{20} = +29.1°$ (c = 1, pyridine).

b. N-formyl-N-(6-methyl-8β-ergolenylmethyl)-1-adamantylamine 16.7 g N-(6-methyl-8β-ergolenylmethyl)-1-adamantylamine are dissolved in 40 ml pure formic acid, and 40 ml acetic acid anhydride is added dropwise at 50° over 5 minutes. The mixture is stirred for a further 10 minutes. 40 ml formic acid and then 40 ml acetic acid anhydride are added. Finally the mixture is stirred at 50° for 45 minutes. The mixture is poured onto ice, made alkaline with potassium hydroxide and extracted with methylene chloride. After further working up a crystalline crude product is obtained which gives after crystallization from methylene chloride/methanol practically colourless crystals of the heading compound. M.Pt. 239°–240° (decomp.); $[\alpha]_D^{20} = +65.4°$ (c = 1, methylene chloride).

EXAMPLE 3

N-methyl-N-(6-methyl-8β-ergolinylmethyl)-1-adamantylamine [process c)]

A solution of 1 g N-methyl-N-(6-methyl-8β-ergolenylmethyl)-1-adamantylamine in 100 ml dimethylformamide is treated with a suspension of 0.75 g prehydrogenated palladium-on-charcoal catalyst (10% by weight Pd) in 50 ml dimethylformamide. The mixture is hydrogenated at room temperature and at normal pressure. After 2 hours the reaction stops, the catalyst is removed by filtration and the filtrate is concentrated to dryness. The residue is crystallized twice from methylene chloride/methanol to give the title compound in free base form as colourless crystals. M.Pt. 243°–245° (decomp.); $[\alpha]_D^{20} = -68.4°$, (c = 1, pyridine).

In analogous manner to that described in Example 1, the following compounds of formula I may be obtained:

a. N-methyl-N-(2-bromo-6-methyl-8β-ergolenylmethyl)-1-adamantylamine and b. N-methyl-N-(2-bromo-6-methyl-8β-ergolinylmethyl)-1-adamantylamine.

The compounds of formula I are useful as sleep-inducing and sleep-prolonging agents, as indicated in standard tests. For example, in the sleep/wake cycle test in rats carried out in accordance with the principles of H. Kleinlogel et al., European J. Pharmacol. 33, 159–163 (1975), an increase in the sleep phase and a decrease in the wake phase was observed on administration p.o. of from 2.5 to 10 mg/kg animal body weight of the compounds.

For this use the dosage will, of course, vary depending on the compound employed, mode of administration and treatment desired. However, in general, satisfactory results are obtained when administered at a daily dosage of from about 0.1 mg to about 10 mg per kg animal body weight, conveniently given as a single dose shortly before retiring to sleep. For the larger mammals, the total daily dosage is in the range from about 1 to about 100 mg.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent.

Such compositions may be in the form of, for example, a solution or a tablet.

What is claimed is:

1. A compound of formula I, wherein
  $R_1$ is alkyl ($C_{1-5}$),
  $R_2$ is alkyl ($C_{1-5}$),
  $R_3$ is hydrogen or halogen, and either each of $R_4$ and $R_5$ is hydrogen, or
  $R_4$ and $R_5$, together, are a bond,
or a pharmaceutically acceptable acid addition salt thereof.

2. A compound of claim 1, wherein $R_3$ is hydrogen.
3. A compound of claim 1, which is N-methyl-N-(6-methyl-8β-ergolenylmethyl)-1-admantylamine.
4. A pharmaceutical composition useful in inducing or prolonging sleep comprising a therapeutically effective amount of a compound according to claim 1, in association with a pharmaceutical carrier or diluent.
5. A method of inducing or prolonging sleep in animals, which comprises administering a therapeutically effective amount of a compound of claim 1 to an animal in need of such treatment.
6. The compound of claim 1 which is N-methyl-N-(2-bromo-6-methyl-8β-ergolenylmethyl)-1-adamantylamine.
7. The compound of claim 1 which is N-methyl-N-(2-bromo-6-methyl-8β-ergolinylmethyl)-1-adamantylamine.

* * * * *